United States Patent
Ramakrishnan et al.

[19]

[11] Patent Number: 5,832,409
[45] Date of Patent: Nov. 3, 1998

[54] AUTOMATED GAS PERMEAMETER

[75] Inventors: T. S. Ramakrishnan, Bethel, Conn.; Sandeep Dhawan, Nanuet, N.Y.; Alphonse Cappiello, Danbury, Conn.

[73] Assignee: Schlumberger Technology Corporation, Ridgefield, Conn.

[21] Appl. No.: 846,101

[22] Filed: Apr. 25, 1997

Related U.S. Application Data

[63] Continuation of Ser. No. 397,348, Mar. 2, 1995, abandoned.

[51] Int. Cl.$^6$ .......................... G01N 15/08; G01N 35/00; G06F 19/00
[52] U.S. Cl. ............................... 702/12; 702/50; 702/47; 702/45; 73/38; 73/152.05; 73/863.01; 73/861; 166/250.02; 166/252.5; 324/376
[58] Field of Search ................................ 73/38, 37, 40, 73/861, 861.01, 152.05, 152.06, 863.01, 863.02, 863.03; 324/376; 166/100, 250.02, 252.5; 250/253, 255; 702/12, 14, 22, 50, 47, 100, 137, 138

[56] References Cited

U.S. PATENT DOCUMENTS

| | | | |
|---|---|---|---|
| 4,191,046 | 3/1980 | Baker et al. | 73/38 |
| 4,198,854 | 4/1980 | Washington et al. | 73/38 |
| 4,679,421 | 7/1987 | Barree | 73/38 |
| 4,864,845 | 9/1989 | Chandler et al. | 73/38 |

OTHER PUBLICATIONS

Gas Permeameter Manual of Porous Materials, Inc. (1992) describing the principles of operation, features and applications of the Gas Permeameter.

*Primary Examiner*—Emanuel Todd Voeltz
*Assistant Examiner*—Tuan Q. Dam
*Attorney, Agent, or Firm*—Keith G. W. Smith; Leonard W. Pojunas

[57] ABSTRACT

An automated gas permeameter measures permeabilities of porous samples, such as rocks, ranging from 0.1 milliDarcys to 10 Darcys within 0.5% under dry and humid conditions. The automated gas permeameter includes a program for estimating a coarse permeablity value. The program uses the coarse value to determine settling time for pressure to reach steady state within 0.1% and optimal operating conditions, such as the setting of mass flow rates imposed on the sample. Operating conditions of the permeameter are set by the program according to the resolution and range of flow controllers, accuracy of a pressure transducer, and the limit of applicability of Darcy's law for a sample.

14 Claims, 9 Drawing Sheets

AUTOMATED GAS PERMEAMETER

This application is a file wrapper continuation of parent application Ser. No. 08/397,348, filed Mar. 2, 1995 now abandoned.

FIELD OF THE INVENTION

The invention relates to an apparatus and method for testing rock samples. More specifically, the invention relates to an automated gas permeameter for testing rock samples from earth formations.

BACKGROUND OF THE INVENTION

Reservoirs of hydrocarbon fluids, such as oil or gas, are usually found in rock formations beneath the Earth's surface. In determining the amount of hydrocarbon fluids which can be produced from a rock formation, it is necessary to know the porosity of the formation. The more porous the formation, the larger the amount of producible fluid. One way to estimate porosity of a formation is with a nuclear logging tool which is winched up a borehole in the rock formation, for example. It is also advantageous to know the permeability of the formation. The more permeable the formation, the easier it is to extract the fluids from the porous rock formation. One way to estimate permeability of a formation is with a geochemical logging tool which is winched up a borehole in the rock formation, for example.

The estimation of permeability of a formation can be verified against core samples taken from that formation. The permeability of the core sample is determined in a laboratory setting using a gas permeameter. Manual laboratory gas permeameters, however, have been cumbersome to use, requiring the operator to look up calibration curves of associated flow meters and to set up the operating environment. To achieve this, the operator must have some prior knowledge about the rock. Because calibration, set-up, and knowledge of the rock are determined by the operator, measurements using manual laboratory gas permeameters are subject to errors caused by the operator.

Semi-automated systems have been proposed. Such systems are semi-automatic in that a computer can be used to set some parameters during the experiment. It also measures the data and finally fits a straight line through the data using least squares. Importantly, the computer still requires input from the operator concerning what the conditions of the experiment are going to be. Such a semi-automatic system does not adapt itself to information about the rock sample under test. The system still needs input and output from an educated operator. Accordingly, the results can be less than accurate.

SUMMARY OF THE INVENTION

The invention concerns an apparatus for determining the permeability of a sample. The apparatus comprises a gas source, and first and second valves for controlling gas flow between the gas source and the sample. A first path connects the gas source to the first and second valves. A second path connects the first and second valves to the sample such that gas flows through the sample. A pressure sensor connects to the second path and produces an output signal indicating pressure in the second path. A controlling means connects to receive the output signal from the pressure sensor and connects to automatically open one of the first and second valves and automatically close the other of the first and second valves according to the output signal. An indicating means indicates permeability of the sample based on the output signal from the pressure sensor.

In one embodiment, the invention relates to an automated gas permeameter for measuring permeabilities of porous samples, such as rocks, under both dry and humid conditions. The invention replaces user knowledge with an automatic and continual interpretation of measurements. Operating conditions are automatically optimized according to pressure and flow rate data, permitting refinement of permeability estimates.

DETAILED DESCRIPTION OF THE INVENTION

The apparatus of this invention automatically measures permeability. The measurement adapts to the properties of the rock sample being investigated. The automated permeameter conducts trial runs which "explore" the rock successively. Initial permeability values are made based on either the transient or preferably its steady response. Pressure and gas flow stability checks make sure that the initial permeability values reflect properties of the rock and not the apparatus itself. Based on the initial estimates an operating environment is chosen for its final set of experiments.

According to this invention, operator intelligence is not at all required. The operator need only drop the sample in the core holder, seal it, and read a permeability value. The apparatus determines the sequence of measurements. In addition, the apparatus enables an automated measurement of permeability that gives negligible error in permeability. For a wide range of permeabilities, we find a repeatability and accuracy of about 0.25%.

Figure 1:
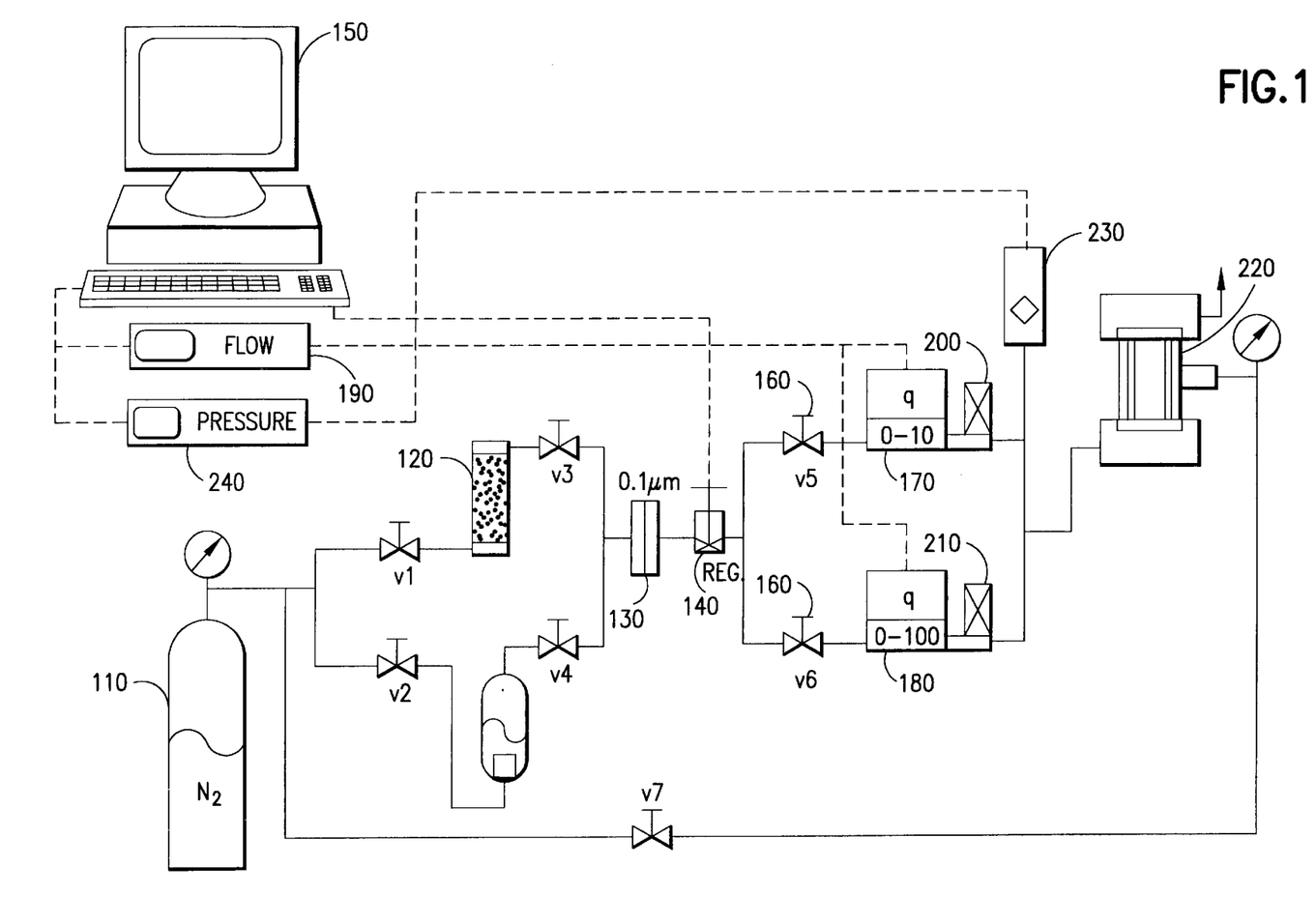
FIG. 1 is a schematic diagram of an automated gas permeameter according to this invention.

FIG. 1 is a schematic diagram of an automated gas permeameter according to this invention. A core sample, such as a sample from a rock formation, is placed in a Hassler-size core holder 220. Nitrogen from a gas cylinder 110 is fed via one line directly to the Hassler core holder 220 in order to maintain pressure on the gland surrounding the core which ensures that gas does not bypass the core. The nitrogen gas is simultaneously fed via another line through Drierite 120 which removes moisture from the gas. The gas then continues through a 0.1 $\mu$m filter 130 which removes any particles that may be suspended in the gas. The gas continues in a first path to a gas flow regulator 140 which is controlled by a computer 150 or other controlling device, such as a microprocessor or dedicated hardware circuit. A second path connects the regulator 140 to the sample. Specifically, after the regulator 140, the gas line splits into two sub-paths which are controlled by two valves 160. The gas flows in parallel through two mass flow meters 170 and 180 with respective ranges of 0–10,000 mm$^3$ and 0–100,000 mm$^3$ at standard conditions (temperature of 273 K, and pressure of 1 atm.). Following the first flow meter 170 is a valve comprising a solenoid 200 which is capable of throttling the flow rate downstream of the flow meter 170. After the second flow meter 180 is a second similar valve comprising a throttling solenoid 210. The regulator 140 provides the proper pressure to the flow meters 170, 180 to eliminate chattering of the valves which would otherwise occur. Both flow meters 170 and 180 along with both solenoids 200 and 210 work in conjunction through a proportional-integral-derivative flow controller 190 which in turn accepts instructions from a computer 150. The two gas lines are then both connected to the core holder 220 and a 0–0.5 MPa strain gauge pressure transducer 230 which measures the pressure downstream of the solenoids 200, 210. The pressure transducer 230 is connected to the pressure controller 240 and the computer 150. The computer 150 includes a display monitor or other device for indicating the value of permeability of the sample under investigation. The computer 150 can comprise a microchip, microprocessor, hardware circuit or main frame computer, if desired.

Figure 2:
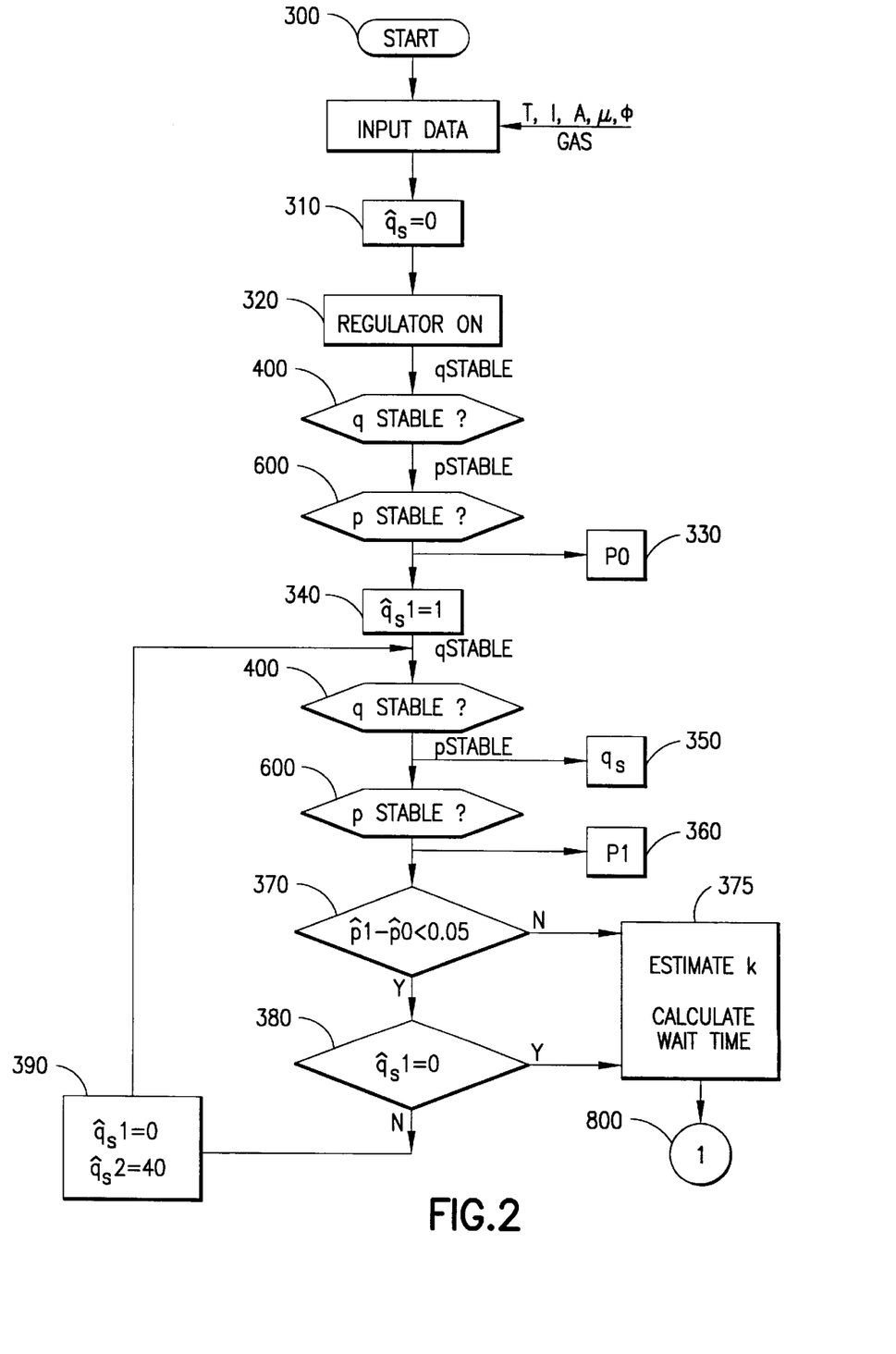
FIGS. 2, 3A, 3B, and 6 are flow charts illustrating the steps of a program for determining of permeability according to this invention.

FIG. 2 is a flow chart illustrating an algorithm for estimating permeability according to this invention. The initial estimate of permeability is calculated by following the steps outlined below. First the length, diameter and porosity (Helium intrusion preferred) of the sample are entered into the program 300 along with temperature and gas type. The initial flow rate is then set to zero, $\hat{q}_{s1}=0$, by the computer at step 310. When the flow rate is zero then $p_o=p_i$ and the system is at atmospheric pressure. Initially $\hat{q}_{s1}$ and $\hat{q}_{s2}$ are zero with the solenoids closed. The computer then energizes the regulator and the downstream pressure is set to 0.25 MPa at step 320. The flow stability is then checked by going to subroutine 400. Once the flow stability requirements have been met the program proceeds to check the pressure stability by processing through subroutine 600. After pressure stability requirements are met the pressure is measured, the initial pressure is $p_0$ at step 330. The program now sets the initial flow rate to 1.5 cc/min. at step 340 by adjusting the solenoid 200 to the proper conditions, solenoid 210 remains closed. The stability of the flow is checked at this point again by the procedure outlined in the flow stability subroutine 400. Once the flow stability requirements are met the flow measurement is recorded, $q_s$ (step 350). The pressure stability is then checked by processing through subroutine 600 after which the pressure, $p_1$ at step 360, is recorded. If $\hat{p}_1-\hat{p}_0$ is greater than 0.05 (in psi) (step 370), expected for a low permeability sample, then an estimate of the permeability, k, and a wait time are calculated at step 375 and the program proceeds to measure an accurate permeability according to step 800. If $\hat{p}_1-\hat{p}_0$ is less than 0.05, expected for a high permeability material, the program proceeds to ask if $\hat{q}_{s1}$, solenoid 200, is set equal to zero (step 380). If $\hat{q}_{s1}$ is equal to zero then an estimate of the permeability, k, and a wait time are calculated at step 375 and again the program proceeds to measure an accurate permeability according to step 800. If $\hat{q}_{s1}$ is not equal to zero, as is the case the first time through, the program then continues and sets $\hat{q}_{s1}$, solenoid 200, to zero and $\hat{q}_{s2}$, solenoid 210, to 40 cc/min. (step 390), for example. After $\hat{q}_{s2}$ has been set to 40 cc/min. the program returns to repeat steps 400, 350, 600, 360, and 370. At step 370, if $\hat{p}_1-\hat{p}_0>0.05$, an estimate of the permeability, k, and a wait time are calculated at step 375. If not, at step 380, $\hat{q}_{s1}$ will be equal to zero, and again an estimate of k and wait time are obtained. This will be the case for extraordinarily high permeabilities. The program then proceeds to measure an accurate permeability according to step 800.

Figure 3A:
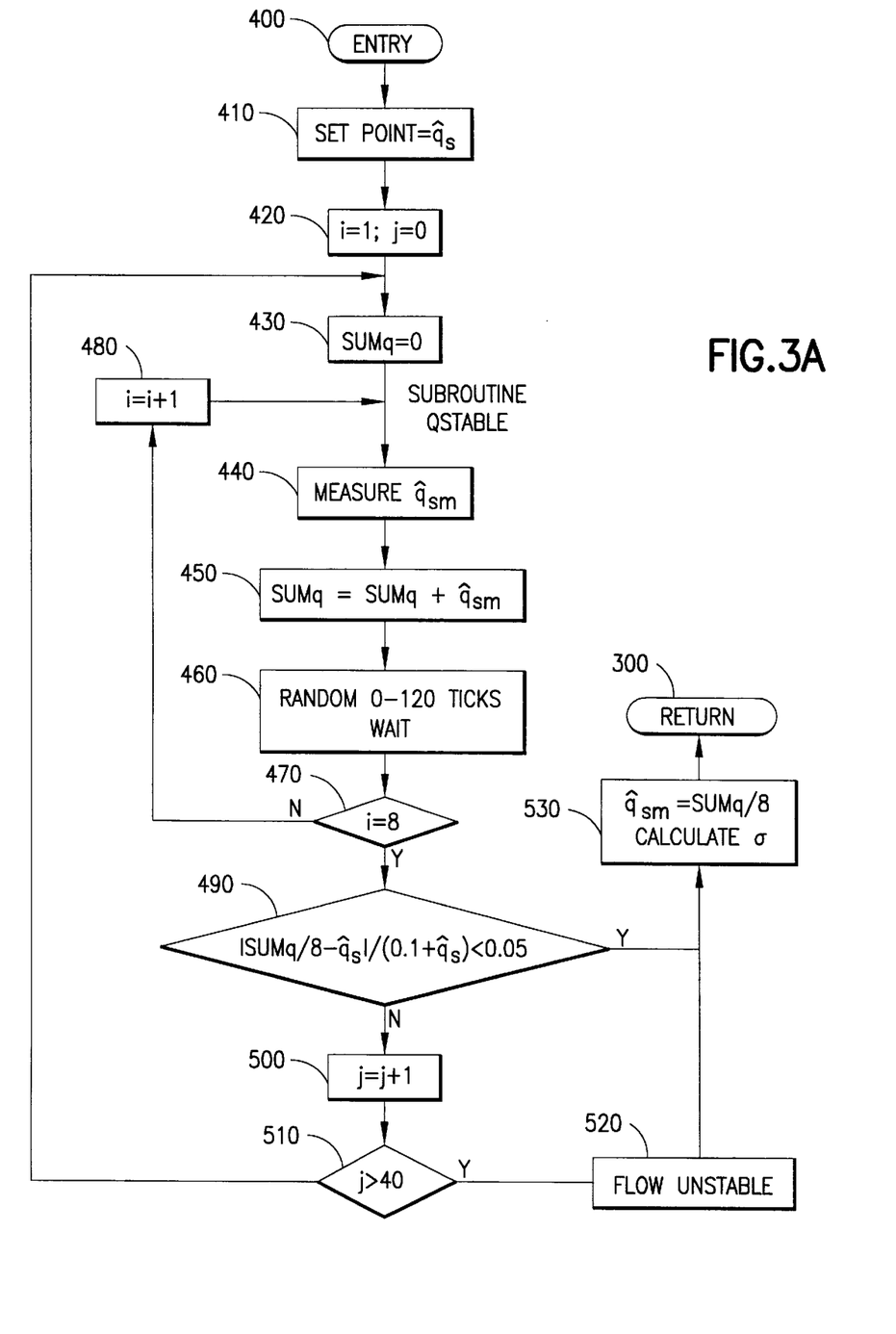

FIG. 3A is a flow chart illustrating a stability check for flow Q. The flow stability is checked according to this Subroutine Q stable 400 which is called in program 300 (FIG. 2). The computer initially sets flow, to designed point (set point $\hat{q}_s$) at step 410, I=1 and J=0 at step 420 and the initial SUMq is set to zero at step 430. The actual flow rate $\hat{q}_{sm}$ is measured at step 440 by the flowmeter and added at step 450 to SUMq of step 430. Flow fluctuations about zero are then checked by first establishing a sampling time. To eliminate any systematic errors due to a fixed sampling time the time between measurements is chosen by randomly selecting between 0 and 120 ticks (⅟₆₀ sec.) at step 460. The flow stability is checked by repeating steps 440 to 460 eight times according to step 470, where each subsequent iteration is I=I+1 at step 480. After the eight flow rate measurements are collected the average flow rate is calculated at step 490.

At step 490 $|SUM\hat{q}/8-\hat{q}s|/(0.1+\hat{q}s)$: is checked to see if it is less than 0.005. If so, then the flow rate $\hat{q}_{sm}$ is equal to SUMq/8 and the error, σ, is calculated at step 530 and the program returns to the estimating k program 300. If the average flow rate of step 490 is greater than 0.005 then the sequence continues by adding 1 to J at step 500 and looping through steps 430 to 500 forty times (step 510) unless the average flow rate is less than 0.005. If the average flow rate is greater than 0.005 after 40 iterations then a warning message "Flow Unstable" is displayed on the computer according to step 520. The program automatically proceeds to step 530 and the flow rate and the error are calculated. The program then returns to estimate the permeability.

Figure 3B:
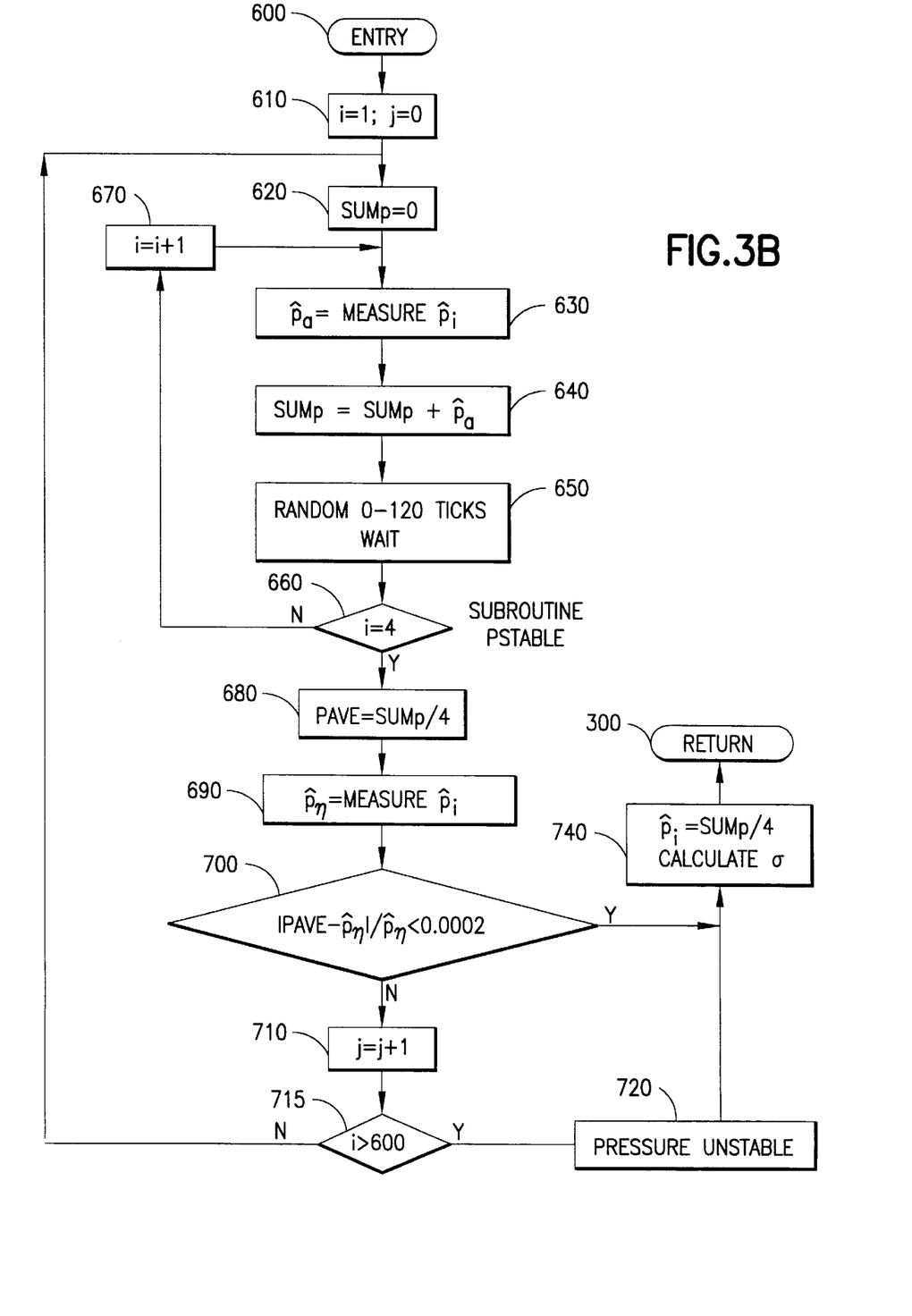

According to FIG. 3B, a pressure stability check is made according to Subroutine P stable 600. The pressure stability is checked by this subroutine and is called in program 300 (FIG. 2). The subroutine first sets I=1 and J=0 at step 610, SUMp is set to zero at step 620 and the pressure $\hat{p}_a$ is set equal to measured pressure $\hat{p}_i$ at step 630. The program next calculates SUMp which is equal to SUMp+$\hat{p}_a$ at step 640. In order to eliminate any systematic errors due to a fixed sampling time the time between measurements is chosen by randomly selecting between 0 and 120 ticks at step 650. The program then checks to see if I=4 at step 660. If I does not equal 4 then the program adds 1 to I at step 670 and repeats steps 630 to 660. If I equals 4 then the average pressure, PAVE, is calculated and is equal to SUMp/4 at step 680. The pressure is then measured again with $\hat{p}_n$=measured $\hat{p}_i$ at step 690. Next the pressure stability is checked by comparing the average pressure with the new pressure, $|PAVE-\hat{p}n|/\hat{p}_n$ at step 700. If it is less than 0.0002 then $\hat{p}_i$ is equal to SUMp/4 and the error, σ, is calculated at step 740. If $|PAVE-\hat{p}n|/\hat{p}_n$ is greater than 0.0002 then the program adds 1 to J at step 710 and loops through steps 620 to 710 until $|PAVE-\hat{p}n|/\hat{p}_n$ <0.0002 or 600 iterations are complete (step 715). If J>600 then the warning message "Pressure Unstable" is displayed on the computer 150 according to step 720 and the program automatically proceeds to calculate $\hat{p}_i$, SUMp/4, and the error, σ at step 740. The subroutine then returns to the permeability estimation program 300.

Figure 4:
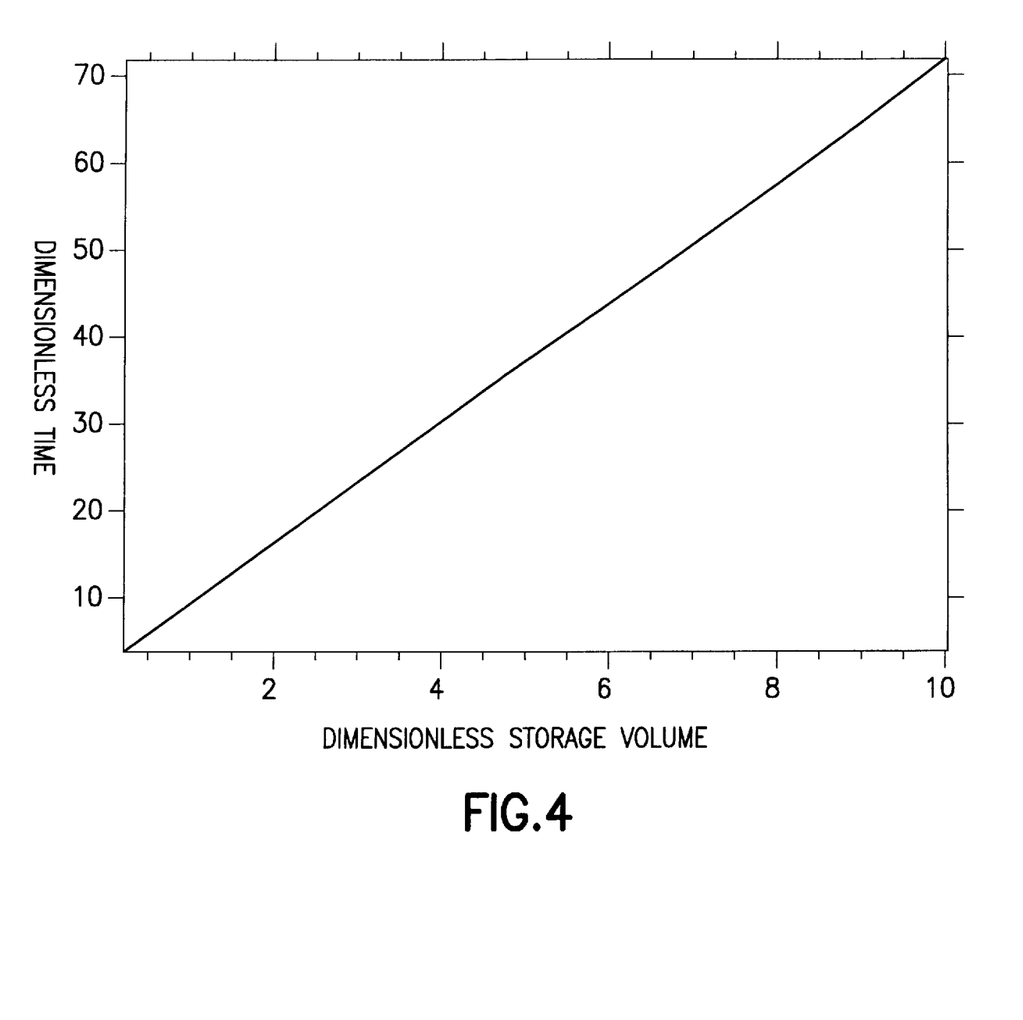
FIG. 4 illustrates waiting time for pressure stability of the apparatus of FIG. 1.

FIG. 4 is a graph indicating waiting time which is plotted as a function of storage volume. Specifically, FIG. 4 indicates time to reach pressure within 99.9% of steady state for pressure to become stable as a function of storage volume of the gas line between throttling solenoids (170,180) and inlet to the core. A waiting time for pressure to become stable is calculated based on the initial estimate of permeability (300). This calculation insures that sufficient time has elapsed before collecting pressure data so that pressure is a function of the sample and not spurious. The waiting time is incorporated into the logic of the program at step 930.

The waiting time is based on the solution for pressure response in a linear core assuming slightly compressible flow. The essential feature of the mathematical solution to pressure diffusion and its asymptotic approximations is that dimensionless time given by $tk/\phi\mu c l^2$ (t=time, k=permeability, $\phi$=porosity, $\mu$=viscosity, c=compressibility of gas, l=length of core) for steady state to occur within 0.1% is proportional to the dimensionless storage volume, $\delta = V_s/\phi l A$, for a wide range of $\delta$ likely to occur. The graphical representation of the solution shown in FIG. 4 illustrates this. With the initial estimate in permeability, k, a wait time for the pressure to stabilize can be quickly calculated. Once the initial estimate of permeability and the pressure stabilization waiting time are established then the program proceeds to measure the final permeability of the sample.

A feature of the pressure response solution is that the permeability of the sample can also be estimated quickly by looking at the early time response. The inventors have found through experimental studies that the two step steady state procedure described above to be very robust.

Figure 5:
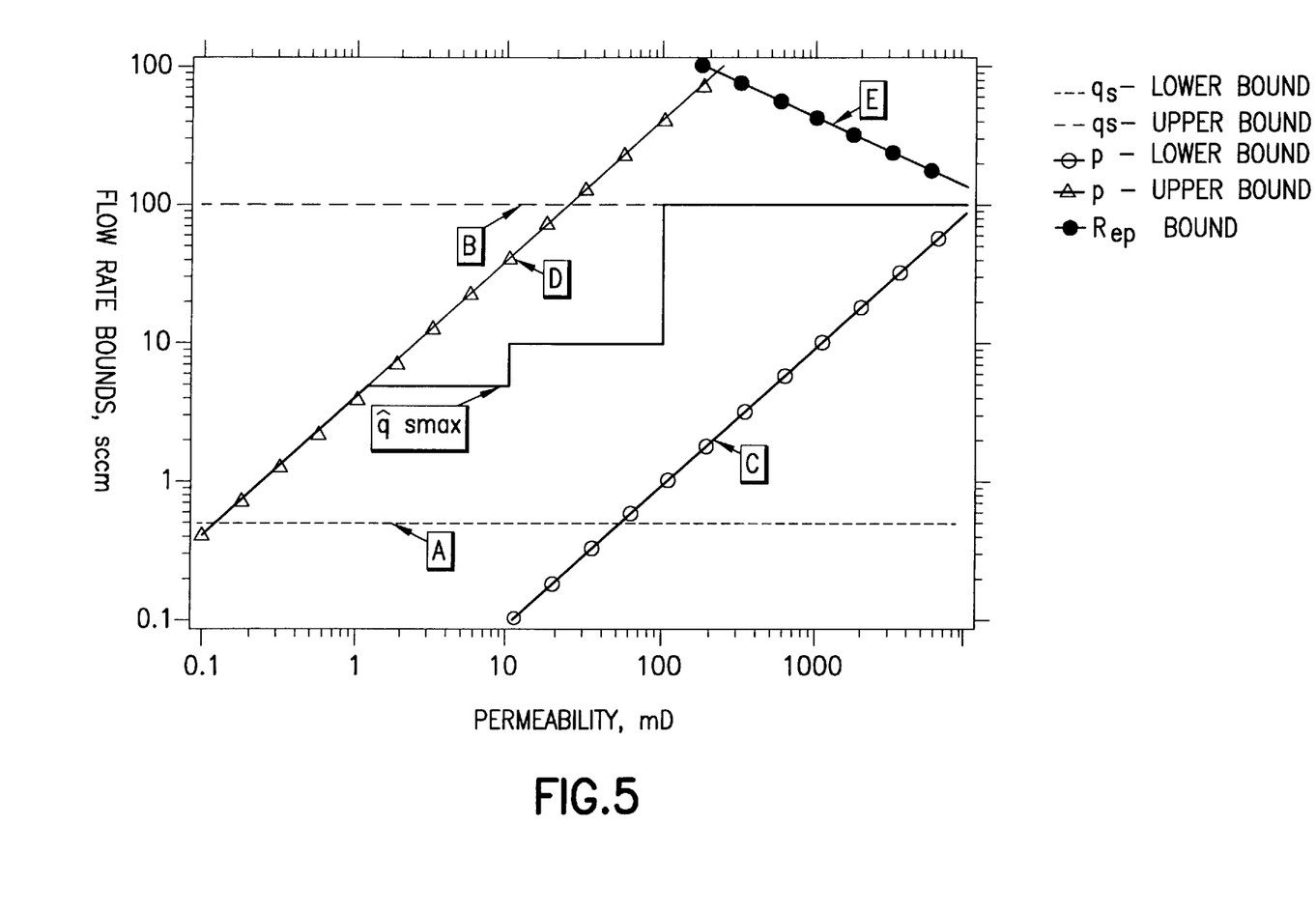
FIG. 5 illustrates maximum flow-rate constraints for the system of FIG. 1.

FIG. 5 illustrates preferred flow rate constraints for the apparatus of FIG. 1. To ensure the repeatability of the reported permeability, several flow rate constraints are considered. These constraints place limits on the flow rates for given ranges of permeability. Assume one-dimensional flow of a gas through a homogenous porous medium. The flowing medium shall be nitrogen, whose critical pressure and temperature are 3.4 MPa and 126 K. By limiting the pressure drop across the core sample to 0.1 MPa, and choosing a nominal operating temperature of 294 K, the compressibility factor is unity within 0.1%. Thus, for local gas density:

$$\rho = \frac{pM}{RT}, \quad (1)$$

where p is the gas pressure, M is the molecular weight, R is the gas constant, and T is the temperature. For accuracy better than 1%, the measurement range for the permeameter shall be $0.0001–10 \,\mu m^2$. With a mean free path of about 0.1 $\mu m$ for nitrogen, Klinkenberg corrections are unimportant. The local form of Darcy's law $$v = -\frac{k}{\mu} \frac{\partial p}{\partial x}, \quad (2)$$

where v is the velocity and $\mu$ is the viscosity may therefore be used for a sufficiently small velocity. x is the distance along the macroscopic direction of flow. Continuity implies that the mass flow rate of gas $\dot{m}$ is a constant. For isothermal conditions, $$\dot{m} = \rho q = \rho_s q_s, \quad (3)$$

where q is the volumetric flow rate equal to vA and the subscript s stands for standard temperature and pressure conditions. A is the cross-sectional flow area. Combining Eqs. 2, 3, 4 and the boundary conditions gives the relationship $$q_s = k \frac{(p_i^2 - p_o^2)AT_s}{2Tp_s\mu l}. \quad (4)$$

Equation 4 forms the basis of our permeability measurement. At zero flow rate the measured pressure is equal to $p_o$. By imposing several flow rates (standard) through the rock and measuring the inlet pressures, an estimate of k may be obtained. The constraints are incorporated into the logic of the computer program driving the experiment. The constraints include the range and resolution of the flow meters and the pressure transducers, the confining pressure used to seal the lateral surface of the rock sample and the limits on Darcy's law. To derive the constraints some typical values are assumed: $\mu$=0.0175 mPas (viscosity of Nitrogen), l=37.5 mm, and A=314.2 mm² (Hassler core sizes) and $p_o$=0.1 MPa (pressure). Equation 4 then reduces to:

$$\hat{q}_s = \frac{\hat{k}(\hat{p}_i^2 - \hat{p}_o^2)}{162}. \quad (5)$$

The ^ denotes units used in the experiment, namely millidarcy for permeability, psi for pressure and standard cc (scc) per minute for flow rate.

The first constraint is a function of the pressure transducer range which is specific to the pressure transducer employed in the experiment. For this experiment the pressure transducer range of 0.5 MPa was chosen so that errors due to hysteresis are minimized when the pressure changes by 0.1 MPa. The resolution of the instrumentation and the transducer together is about 3.4 Pa and based on trial runs, we have estimated that a change of 68 Pa can be reliably obtained. This means that the maximum flow rate used in a set of five rates should give a pressure drop greater than 340 Pa, which leads to boundary C in FIG. 5:

$$\hat{q}_s > 0.0091 \hat{k}. \quad (6)$$

The second constraint is a function of the confining pressure used to seal the lateral surface of the rock sample. To assume the ideal gas law of Equation 1, we limit the pressure drop to 0.11 MPa. Since the sealing pressure is 0.5 MPa, gauge, this helps to ensure that no gas will bypass the sample. Thus, from Equation 6 above, the upper bound on pressure drop leads to boundary D in FIG. 5:

$$\hat{q}_s < 4.1\hat{k}. \quad (7)$$

The third constraint arises from the range and resolution of the flow meters and controllers. With two separate flow meters and controllers this leads to boundaries A and B in FIG. 5:

$$0.5 < \hat{q}_s < 100. \quad (8)$$

The fourth restriction is that the flow rate should be sufficiently small for Darcy's law to be valid. This can be approximated by estimating the Reynolds number, $Re_p$. Based on the Kozeny-Carmen equation, the permeability for spherical bead packs is $$k \approx \frac{K}{4} d_p^2$$

where K has a magnitude of $10^{-3}$. Using this estimate, and conservatively keeping $Re_p<0.1$, it may be shown that this restriction leads to boundary E in FIG. 5:

$$\hat{q}_s < \frac{13300}{\sqrt{\hat{k}}}. \quad (9)$$

The constraints outlined above, and depicted in FIG. 5, define an area within curves A–E which impose a maximum flow rate during the course of the experiment. The choice of flow meters is now obvious. Ranges higher than $\hat{q}_s$=100 may lead to measurement nonlinearities. Among these curves, to ensure accuracy, it is advisable to lie in the middle of lines C and D. Through several trial runs, we finally settled upon a path shown by $\hat{q}_{sma}$ to be the maximum rate set for a given estimate of permeability obtained in step 300. In the final determination of permeability 800, it is this maximum flow rate and the initial estimate of permeability that are incorporated into the logic of the experiment (See FIG. 6): for tight permeabilities (0.1<k<1), $\hat{q}_{smax}$=4.0k scc/min. (860); low permeabilities (1<k<10), $\hat{q}_{smax}$=5 scc/min. (870), for medium permeabilities (10<k<100), $\hat{q}_{smax}$=10 scc/min. (880) and for high permeabilities (100<k<10,000), $\hat{q}_{smax}$=100 scc/min. (890).

Figures 6, 6A:
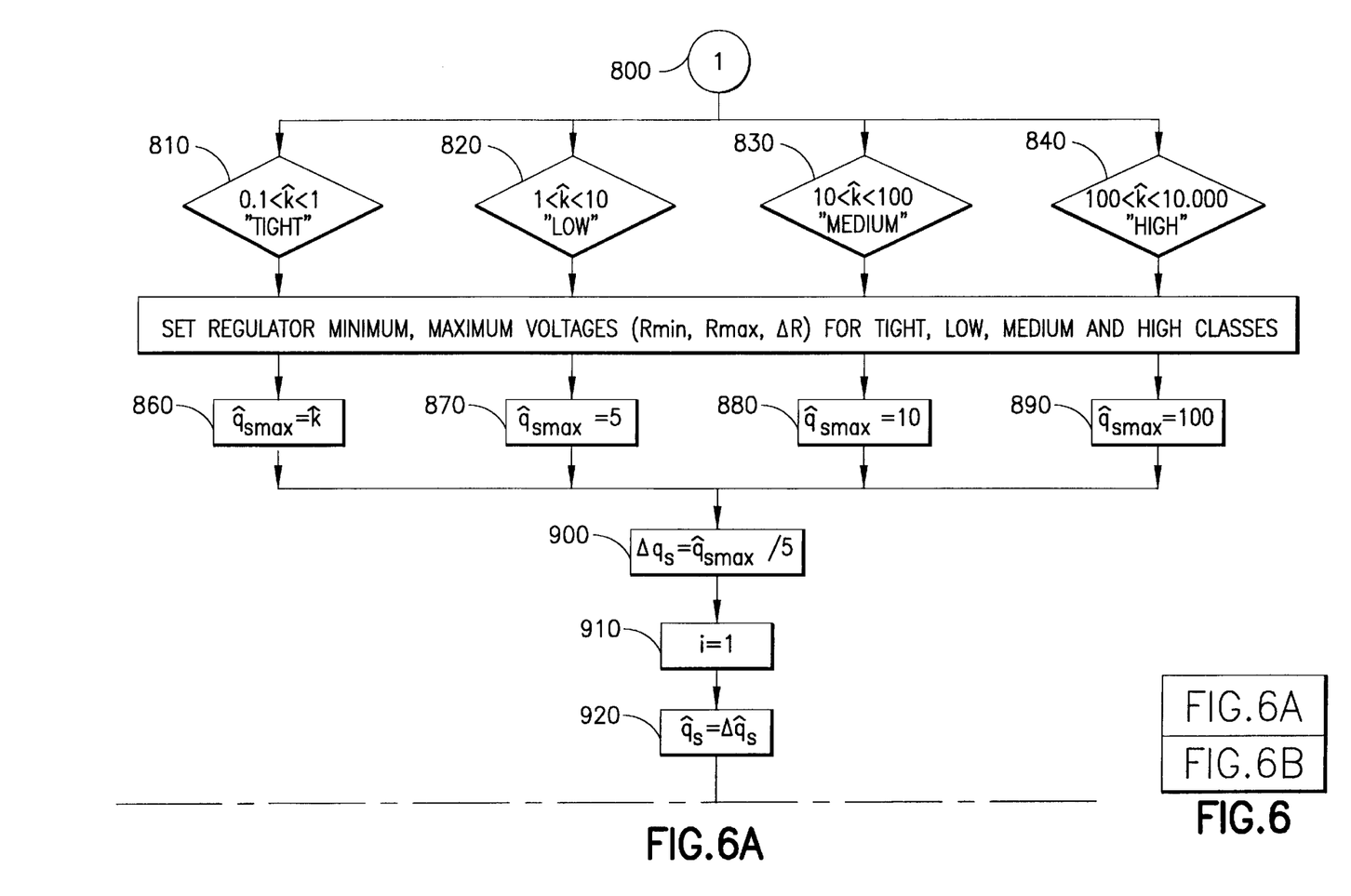
Figure 6B:
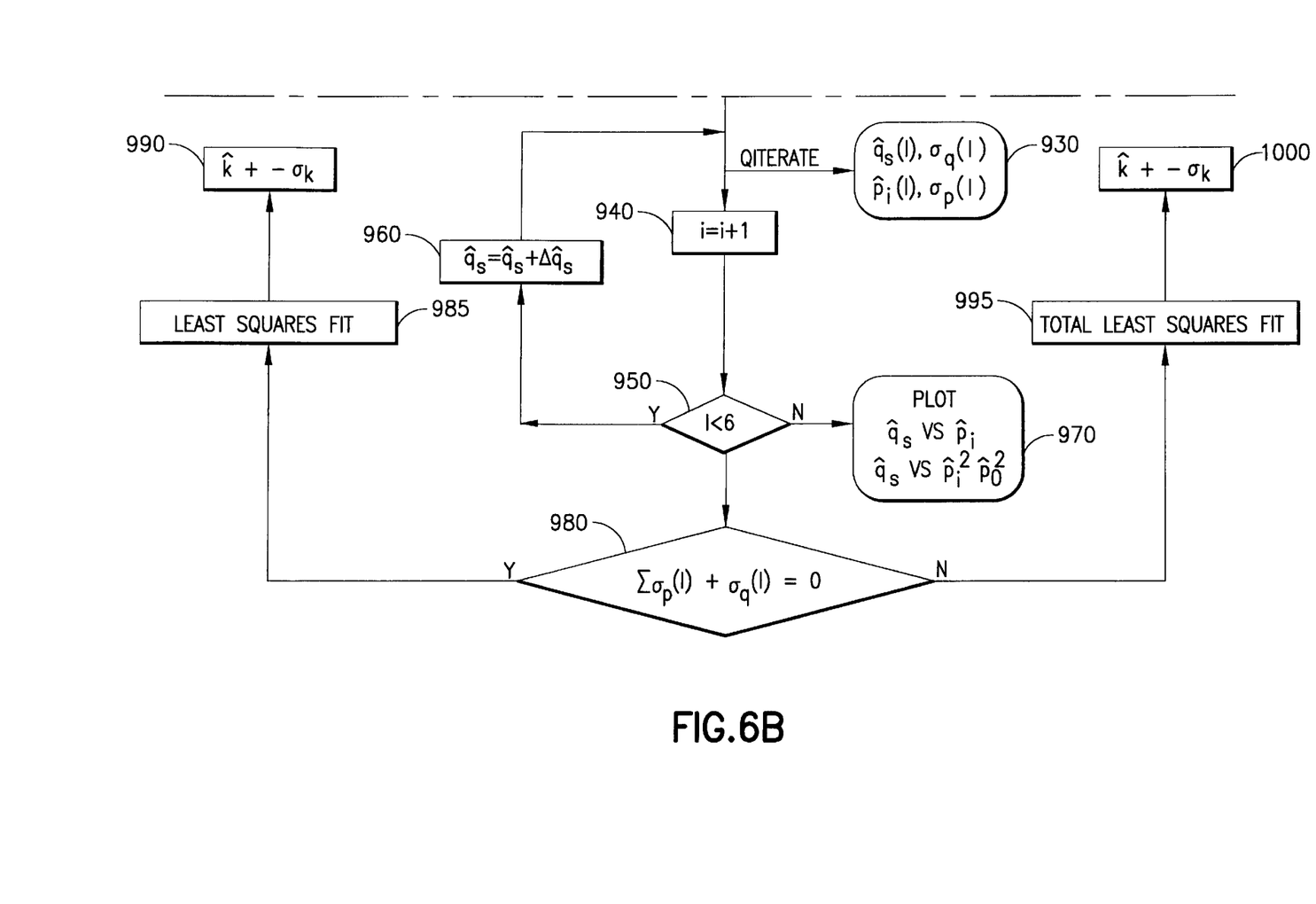

FIG. 6 is a flow chart illustrating steps for measuring tight, low, medium and high permeabilities. Once permeability estimate and waiting time are established (step 300) then a more accurate measurement of permeability is made. First, the estimated permeability is categorized into one of four classes, tight 0.1<k<1 mD (step 810), low 1<k<10 mD (step 820), medium 10<k<100 mD (step 830) and high 100<k<10,000 mD (step 840). Next, the maximum flow rate for each class is assigned according to FIG. 5. (Steps 860, 870, 880, 890) For a tight sample the maximum flow rate is 4.0 scc/min., qsmax=4.0 scc/min. (step 860), for a low permeability sample the maximum flow rate is 5 scc/min., qsmax=5 scc/min. (step 870), for a medium permeability sample the maximum flow rate is 10 scc/min. (step 880), $\hat{q}$smax=10 scc/min. (step 880) and for a high permeability sample the maximum flow rate is 100 scc/min., $\hat{q}$smax=100 scc/min. (step 890). The maximum flow rate, qsmax, is then divided into five equal steps, $\hat{q}_s = \hat{q}_{smax}/5$ (step 900). To cycle through the five flow rates the computer first assigns I=1 (step 910) and $\hat{q}_s = \Delta\hat{q}_s$ (step 920). The regulator pressure is then set to minimize fluctuations in flow rate. The appropriate flow controller and solenoid are adjusted to the flow rate specified in step 920. At each flow rate, $\hat{q}_s$, both the stabilized flow (step 400) and the stabilized pressure (step 600) are recorded along with their variances (step 930). The program proceeds to add 1 to I (step 940) and if I is less than 6 (step 950) then a new flow rate is established, $\hat{q}_s = \hat{q}_s + \Delta\hat{q}_s$ (step 960). The regulator, the flow controller and the solenoid are then set according to the updated flow rate (step 960) and steps 930, 940, 950 and 960 are repeated until I is not less than 6. After the five flow rates have been set and flow and pressure measurements are made then the computer displays a plot of $\hat{q}_s$ vs. $\hat{q}_i$ and $\hat{q}_s$ vs. $\hat{p}_i^2 - \hat{p}_o^2$ (step 970). If the sum of all the variances is negligible, (step 980), then a least squares algorithm (step 985) is used to calculate the permeability and its estimated variance from Equation 4 (step 990). If the sum of all the variances, $\Sigma\sigma p(I)+\sigma q(I)$, is not negligible then a total least squares algorithm (see *Numerical Recipes,* Press et al., 1993) which accounts for errors in both the flow rates and pressures is used to calculate the permeability and its estimated variance from Equation 5 (step 1000).

Accordingly, a method is presented for determining the permeability of a sample. The steps comprise flowing gas from a source 110 in a first path connecting the source 110 to a gas flow regulator 140 and flowing gas in a second path connecting the regulator 140 to the sample such that gas flows through the sample. Gas flow in the second path is controlled with first 160 and second 170 valves in the second path. An output signal indicates pressure in the second path is produced with a pressure sensor connected to the second path. The output signal from the pressure sensor 230 is received by a controlling means including flow and pressure indicators 190, 240 and computer 150 connected to automatically operating the regulator 140 and to automatically open the first valve 170 and automatically close the second valve if the output signal from the pressure sensor indicates a pressure level in the second path below a set threshold, and to automatically close the first valve 170 and automatically open the second valve 180 if the output signal indicates a pressure level above the set threshold. A computing means determines plural, time-random pressure levels used in determining a pressure stability of the second path, and automatically opening and automatically closing the first and second valves according to the pressure stability of the second path, the second path comprising two parallel sub-paths connecting the regulator and the sample, each sub-path separately including one of the first and second valves. Permeability of the sample is indicated based on the output signal from the pressure sensor.

Additionally, a first value of a flow rate of gas in the second path is determined; the first value of the flow rate is cyclically incrementing, adjusting the gas flow regulator and controlling means according to the subsequent value of the flow rate, replacing the first value of the flow rate with the subsequent value of the flow rate and the incrementing steps are repeated a set number of times (e.g., five). Pressure and flow rate of gas in the second path are measured upon incrementing values of the flow rate the set number of times. The measured pressure and flow rate are used to indicate permeability of the sample.

Figure 7:
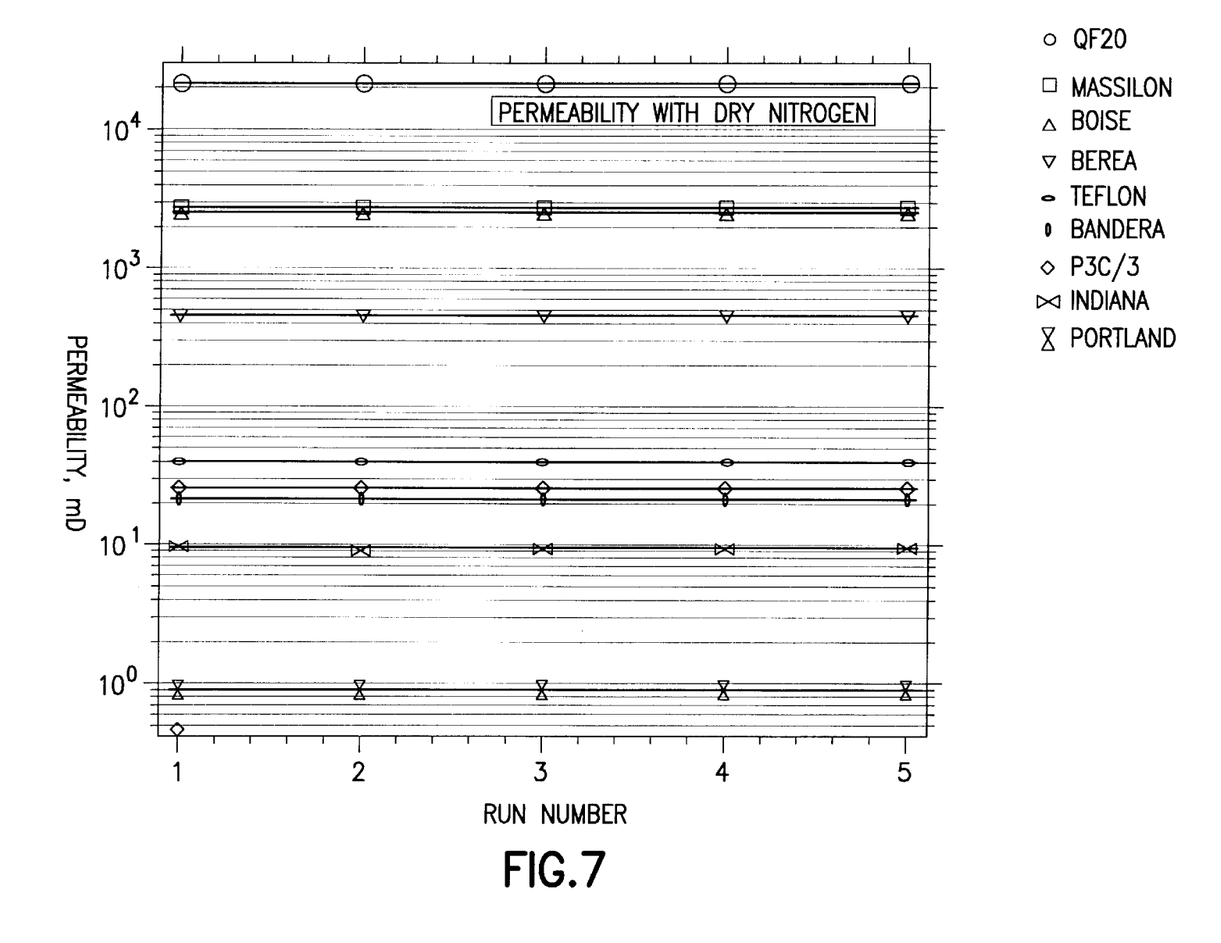
FIG. 7 illustrates the accuracy and repeatability with which permeability can be measured using the method and apparatus of this invention.

FIG. 7 illustrates the accuracy and repeatability with which permeability can be measured using the method and apparatus of this invention. Dry nitrogen permeability in milliDarcys is plotted against a test run number, 1–5, for nine synthetic and natural samples. The flat horizontal plots of permeability for each sample indicate that the measurement of permeability is consistent throughout the test run. Sample QF20 is glass bonded silica. Massilon, Boise, Berea, and Bandera are sandstones. Teflon is a synthetic (hydophobic). P3C/3 is a ceramic (hydrophobic). Indiana is a limestone, and Portland is a red sandstone.

To avoid variation due to atmospheric humidity variation, all the samples were kept in a vacuum oven at 353 K degrees for a minimum of twelve hours. The samples were then transferred to a silica gel desicator and brought to atmospheric pressure and temperature of 21±0.5 C. degrees. The five permeability runs were then run in sequence. Because the variation in permeability calculated by the system was very small, the standard deviation as error bars barely show up in the plot of FIG. 7.

OPERATING PROCEDURES

Set-up Procedures

1. Core sample to standard Hassler-size (3.75 cm long, 2.0 cm diameter) according to the size of core holder.

2. Measure porosity of the sample (Helium Intrusion preferred), necessary to calculate wait time.

3. Humidity control of sample

Dry sample in a vacuum oven (353 K, 12 hrs)

Cool the sample, and transfer the sample to a dessicator (atm P and room T).

4. Clean the core holder by blowing air over the rubber sleeve.

5. Warm up the system including the flow controllers by turning on the system for 0.5 hr.

6. Load the sample into the core holder.

7. Open the direct-line valve to the gas source, such as N2.

8. Close valves 160.

9. The pots on the flow meter should be adjusted to read zero in the flow meter.

10. Open valves 160.

11. Open the valve in the direct line and set the desired boot pressure by applying pressure to the rubber sleeve surrounding the sample.

Run Gas Perm Program, the Automated Part of the Experiment

Run program Gas Perm. See flow chart 300, FIG. 3a, and Schematic of Automated Permeameter, FIG. 2; sub-routines 400 and 600, pressure and flow stability checks, FIG. 3c; Calculating Pressure Stability Wait Time section, FIG. 4; final permeability flow chart 800, FIG. 3b, and maximum flow rate constraints section, FIG. 1.

1. The following inputs are entered into the program, step 300 (FIG. 3a):
   - core length, core diameter, core porosity
   - Gas viscosity, temperature, storage volume, gas compressibility factor (GCF)
   - Choose Least squares or total least squares algorithm. Least squares is the default.
   - Check the default settings for input voltage to regulator, channels for flow meter, the channel connecting the pressure transducer and calibration constants for the transducer. These default settings are highly recommended.

2. The program then follows the steps outlined in flow chart for estimating permeability measurement algorithm 300 (FIG. 3a).
   - This program calls subroutines 400 and 600, flow and pressure stability checks (FIG. 3c).
   - Slight fluctuations in zero flow rate setting might cause a warning window to appear.
   - The output of this program is an estimate of k and the wait time needed for pressure to become stable (See Calculating Pressure Stability Wait Time section, FIG. 4).

3. The program continues and follows steps outlined in the flow chart for final permeability measurement algorithm 800, FIG. 3b.
   - The logic steps followed in this flow chart are reviewed in the Maximum Flow Rate Constraints section, FIG. 1.
   - This program calls subroutines 400 and 600, flow and pressure stability checks (FIG. 3c).
   - The output of this program is permeability along with the error of the measurement.

We claim:

1. A method for automatically determining the permeability of a sample, wherein all determining steps have been coordinated and controlled automatically by a computer or the like controlling device, comprising:
   - controlling and flowing gas to the sample at a first predetermined flow rate;
   - controlling and checking that the gas flow rate and pressure meet stability requirements, prior to obtain a stabilized first pressure:
   - automatically measuring the pressure of the gas to obtain a stabilized first pressure;
   - if the stabilized first pressure is greater than a predetermined first value, indicating a low permeability sample, and for estimating the permeability of the sample;
   - automatically calculating a wait time as a function of the estimated permeability and storage volume; and
   - automatically marking a more accurate measurement of the permeability.

2. The method according to claim 1, further comprising:
   - if the stabilized first pressure is less than the predetermined first value, flowing gas to the sample at a second predetermined flow rate higher than the first flow rate;
   - controlling and checking that the gas flow rate and pressure meet stability requirements, prior to obtain a stabilized second pressure;
   - automatically measuring the pressure of the gas to obtain a stabilized second pressure;
   - if the stabilized second pressure is greater than a second predetermined value, indicating a second, higher permeability, and for estimating the second permeability of the sample;
   - automatically calculating a second wait time based on the second estimated permeability; and
   - automatically marking a more accurate measurement of the permeability.

3. The method according to claim 2, in which the step of making a second, more accurate measurement of the permeability comprises the steps of:
   - categorizing the estimated permeability into one of a plurality of classes;
   - assigning a maximum flow rate for each class in accordance with predetermined constraints;
   - dividing the maximum flow rate into a plurality of steps;
   - cycling through the plurality of flow rate steps, by flowing gas into the sample at each of said flow rate steps; and
   - automatically indicating thus-measured permeability.

4. The method according to claim 1, in which the step of calculating the wait time uses dimensionless time, including the estimated permeability, and dimensionless storage volume.

5. The method according to claim 2, in which the step of calculating the second wait time uses dimensionless time, including the second estimated permeability, and dimensionless storage volume.

6. The method according to claim 4 or 5, in which the dimensionless time is given by $$tk/\phi\mu cl^2$$

and dimensionless storage volume is given by $$\delta = V_s/\phi lA$$

where t=time, k=permeability, $\phi$=porosity, $\mu$=viscosity, c=compressibility of gas, l=length of the sample, $\delta$=the dimensionless storage volume $V_s$=the storage volume, and A=the cross section of the sample.

7. The method according to claim 1, in which the step of making a more accurate measurement of the permeability comprises the steps of:
   - categorizing the estimated permeability into one of a plurality of classes;
   - assigning a maximum flow rate for each class in accordance with predetermined constraints;
   - dividing the maximum flow rate into a plurality of steps;
   - cycling through the plurality of flow rate steps, by flowing gas into the sample at each of said flow rate steps; and
   - automatically indicating thus-measured permeability.

8. The method according to claim 7 or 3, in which the predetermined constraints comprise first, second, third and fourth constraints;
   - and in which the pressure is measured with a pressure transducer and the first constraint is a function of the range of said pressure transducer;
   - and in which the sample has a lateral surface which is sealed by a confining pressure, and the second constraint is a function of said confining pressure;
   - and in which the gas flow rate is determined by meters and controllers, and the third constraint is a function of the range and resolution of said meters and controllers;

and in which the fourth constraint is hat the flow rate should be sufficiently small for Darcy's law to be valid.

9. The method according to claim 1 or 2, in which the step of checking pressure stability comprises determining plural, time-random pressure levels.

10. The method according to claims 1 or 2, in which the predetermined flow rates are constrained between approximately 0.5 sccm and approximately 100 sccm.

11. Apparatus for automatically determining the permeability of a samples wherein all determining steps have been coordinated and controlled automatically by a computer or the like controlling device, comprising:

means for controlling and flowing gas to the sample at a first predetermined flow rate;

means for automatically controlling and checking that the gas flow rate and pressure meet stability requirements, prior to obtain a stabilized first pressure;

means for automatically measuring the pressure of the gas to obtain a stabilized first pressure;

means for automatically determining if the stabilized first pressure is greater than a predetermined first value, indicating a low permeability sample, and for estimating the permeability of the sample;

means for automatically calculating a wait time as a function of the estimated permeability and storage volume; and means for automatically marking a more accurate measurement of the permeability.

12. Apparatus according to claim 11, further comprising:

means for determining if the stabilized first pressure is less than the predetermined first value, and for flowing gas to the sample at a second predetermined flow rate higher than the first flow rate;

means for automatically controlling and checking that the gas flow rate and pressure meet stability requirements, prior to obtain a stabilized second pressure;

means for automatically measuring the pressure of the gas to obtain a stabilized second pressure;

means for automatically determining if the stabilized second pressure is greater than a second predetermined value, indicating a second, higher permeability, and for estimating the second permeability of the sample;

means for automatically calculating a second wait time based on the second estimated permeability; and means for automatically marking a second, more accurate measurement of the permeability.

13. Apparatus according to claim 12, in which the means for making a second, more accurate measurement of the permeability comprises:

means for categorizing the estimated permeability into one of a plurality of classes;

means for assigning a maximum flow rate for each class in accordance with predetermined constraints;

means for dividing the maximum flow rate into a plurality of steps;

means for cycling through the plurality of flow rate steps, by flowing gas into the sample at each of said flow rate steps; and means for automatically indicating thus-measured permeability.

14. Apparatus according to claim 11, in which the means for making a more accurate measurement of the permeability comprises:

means for categorizing the estimated permeability into one of a plurality of classes;

means for assigning a maximum flow rate for each class in accordance with predetermined constraints;

means for dividing the maximum flow rate into a plurality of steps; means for cycling through the plurality of flow rate steps, by flowing gas into the sample at each of said flow rate steps; and means for automatically indicating thus-measured permeability.

* * * * *